(12) United States Patent
Spross et al.

(10) Patent No.: US 8,511,379 B2
(45) Date of Patent: Aug. 20, 2013

(54) DOWNHOLE X-RAY SOURCE FLUID IDENTIFICATION SYSTEM AND METHOD

(75) Inventors: Ronald L. Spross, Humble, TX (US); Jerome Allen Truax, Houston, TX (US); Paul F. Rodney, Spring, TX (US); Daniel David Gleitman, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 295 days.

(21) Appl. No.: 12/682,906

(22) PCT Filed: Nov. 13, 2008

(86) PCT No.: PCT/US2008/083422
§ 371 (c)(1),
(2), (4) Date: Jun. 2, 2010

(87) PCT Pub. No.: WO2009/064899
PCT Pub. Date: May 22, 2009

(65) Prior Publication Data
US 2010/0236776 A1 Sep. 23, 2010

Related U.S. Application Data

(60) Provisional application No. 60/987,729, filed on Nov. 13, 2007.

(51) Int. Cl.
*E21B 49/10* (2006.01)
*E21B 47/00* (2006.01)
*G01V 5/12* (2006.01)

(52) U.S. Cl.
USPC ... 166/264; 166/100; 166/250.17; 250/269.1; 250/266; 378/89; 73/152.55; 73/152.24

(58) Field of Classification Search
USPC ............... 166/264, 100, 250.17, 169, 191; 175/50, 59, 40, 58; 73/152.55, 65.45, 152.17, 73/152.26, 152.18, 152.23, 152.24, 152.28; 250/301, 269.1, 266, 264, 265, 269; 378/88, 378/89, 124
See application file for complete search history.

(56) References Cited

U.S. PATENT DOCUMENTS

| | | | |
|---|---|---|---|
| 4,490,609 | A | 12/1984 | Chevalier |
| 4,980,642 | A | 12/1990 | Rodney |
| 5,171,986 | A | 12/1992 | Loomis et al. |
| 5,451,779 | A | 9/1995 | Spross et al. |
| 5,680,431 | A * | 10/1997 | Pietras et al. .......... 378/119 |
| RE36,012 | E | 12/1998 | Loomis et al. |
| 6,220,371 | B1 | 4/2001 | Sharma et al. |
| 6,543,281 | B2 | 4/2003 | Pelletier et al. |
| 6,619,395 | B2 | 9/2003 | Spross |

(Continued)

OTHER PUBLICATIONS

PCT/US2008/083422 International Search Report and Written Opinion, May 26, 2009.

*Primary Examiner* — Jennifer H Gay
(74) *Attorney, Agent, or Firm* — Conley Rose, P.C.

(57) ABSTRACT

A method and system for determining a property of a sample of fluid in a borehole. A fluid sample is collected in a downhole tool. While collecting, X-rays are transmitted proximate the fluid from an X-ray source in the tool and an X-ray flux that is a function of a property of the fluid is detected. The detected X-ray flux data is processed to determine the property of the fluid.

40 Claims, 3 Drawing Sheets

(56) References Cited

U.S. PATENT DOCUMENTS

| | | | |
|---|---|---|---|
| 6,918,293 B2 | 7/2005 | Moake et al. | |
| 6,957,145 B2 | 10/2005 | Spross | |
| 7,075,062 B2* | 7/2006 | Chen et al. | 250/269.1 |
| 7,128,144 B2 | 10/2006 | Fox et al. | |
| 7,178,591 B2 | 2/2007 | Del Campo et al. | |
| 7,207,215 B2 | 4/2007 | Spross et al. | |
| 7,379,180 B2* | 5/2008 | Vannuffelen et al. | 356/326 |
| 7,461,547 B2* | 12/2008 | Terabayashi et al. | 73/152.55 |
| 7,507,952 B2* | 3/2009 | Groves et al. | 250/269.1 |
| 7,508,506 B2* | 3/2009 | Christian et al. | 356/319 |
| 7,728,971 B2* | 6/2010 | Christian et al. | 356/319 |
| 7,807,962 B2* | 10/2010 | Waid et al. | 250/269.1 |
| 7,948,620 B2* | 5/2011 | Christian et al. | 356/319 |
| 8,109,140 B2* | 2/2012 | Tustin et al. | 73/152.24 |
| 2003/0106993 A1* | 6/2003 | Chen et al. | 250/269.1 |
| 2004/0216874 A1* | 11/2004 | Grant et al. | 166/264 |
| 2006/0243047 A1 | 11/2006 | Terabayashi et al. | |
| 2007/0186639 A1 | 8/2007 | Spross et al. | |
| 2007/0252080 A1 | 11/2007 | Truax | |
| 2007/0274443 A1* | 11/2007 | Groves et al. | 378/54 |
| 2008/0073078 A1* | 3/2008 | Sherwood | 166/264 |
| 2008/0078544 A1* | 4/2008 | Christian et al. | 166/264 |
| 2009/0078036 A1* | 3/2009 | Terabayashi et al. | 73/152.55 |
| 2009/0103087 A1* | 4/2009 | Christian et al. | 356/326 |
| 2009/0126996 A1* | 5/2009 | Villareal et al. | 175/50 |
| 2009/0314077 A1* | 12/2009 | Tustin et al. | 73/152.24 |
| 2010/0192684 A1* | 8/2010 | Wu et al. | 73/152.55 |
| 2010/0206063 A1* | 8/2010 | Fujisawa et al. | 73/152.24 |
| 2010/0236776 A1* | 9/2010 | Spross et al. | 166/250.02 |
| 2010/0282959 A1* | 11/2010 | Dong et al. | 250/269.1 |
| 2010/0313647 A1* | 12/2010 | Terabayashi et al. | 73/152.55 |
| 2012/0055242 A1* | 3/2012 | Tustin et al. | 73/152.24 |
| 2012/0086454 A1* | 4/2012 | Kumar | 324/324 |

* cited by examiner

DOWNHOLE X-RAY SOURCE FLUID IDENTIFICATION SYSTEM AND METHOD

CROSS-REFERENCE TO RELATED APPLICATIONS

This application is a 35 U.S.C. §371 national stage application of PCT/US2008/083422 filed 13 Nov. 2008, which claims the benefit of U.S. Provisional Patent Application No. 60/987,729 filed 13 Nov. 2007, both of which are incorporated herein by reference in their entireties for all purposes.

STATEMENT REGARDING FEDERALLY SPONSORED RESEARCH OR DEVELOPMENT

Not Applicable.

BACKGROUND

During the drilling and completion of oil and gas wells, it may be necessary to engage in ancillary operations, such as monitoring the operability of equipment used during the drilling process or evaluating the production capabilities of formations intersected by the wellbore. For example, after a well or well interval has been drilled, zones of interest are often tested to determine various formation properties such as permeability, fluid type, fluid quality, formation temperature, formation pressure, bubblepoint and formation pressure gradient. These tests are performed in order to determine whether commercial exploitation of the intersected formations is viable and how to optimize production.

Wireline formation testers (WFT) and drill stem testing (DST) have been commonly used to perform these tests. The basic DST test tool consists of a packer or packers, valves or ports that may be opened and closed from the surface, and two or more pressure-recording devices. The tool is lowered on a work string to the zone to be tested. The packer or packers are set, and drilling fluid is evacuated to isolate the zone from the drilling fluid column. The valves or ports are then opened to allow flow from the formation to the tool for testing while the recorders chart static pressures. A sampling chamber traps clean formation fluids at the end of the test. WFTs generally employ the same testing techniques but use a wireline to lower the test tool into the well bore after the drill string has been retrieved from the well bore, although WFT technology is sometimes deployed on a pipe string. The wireline tool typically uses packers also, although the packers are placed closer together, compared to drill pipe conveyed testers, for more efficient formation testing. In some cases, packers are not used. In those instances, the testing tool is brought into contact with the intersected formation and testing is done without zonal isolation across the axial span of the circumference of the borehole wall.

WFTs may also include a probe assembly for engaging the borehole wall and acquiring formation fluid samples. The probe assembly may include an isolation pad to engage the borehole wall. The isolation pad seals against the formation and around a hollow probe, which places an internal cavity in fluid communication with the formation. This creates a fluid pathway that allows formation fluid to flow between the formation and the formation tester while isolated from the borehole fluid.

In order to acquire a useful sample, the probe must stay isolated from the relative high pressure of the borehole fluid. Therefore, the integrity of the seal that is formed by the isolation pad is critical to the performance of the tool. If the borehole fluid is allowed to leak into the collected formation fluids, a non-representative sample will be obtained and the test will have to be repeated.

Examples of isolation pads and probes used in WFTs can be found in Halliburton's DT, SFTT, SFT4, and RDT tools. Isolation pads that are used with WFTs are typically rubber pads affixed to the end of the extending sample probe. The rubber is normally affixed to a metallic plate that provides support to the rubber as well as a connection to the probe. These rubber pads are often molded to fit within the specific diameter hole in which they will be operating.

With the use of WFTs and DSTs, the drill string with the drill bit must be retracted from the borehole. Then, a separate work string containing the testing equipment, or, with WFTs, the wireline tool string, must be lowered into the well to conduct secondary operations. Interrupting the drilling process to perform formation testing can add significant amounts of time to a drilling program.

The formation pressure measurement accuracy of drill stem tests and, especially, of wireline formation tests may be affected by filtrate invasion and mudcake buildup because significant amounts of time may have passed before a DST or WFT engages the formation. Mud filtrate invasion occurs when the drilling mud fluids displace formation fluids. Because the mud filtrate ingress into the formation begins at the borehole surface, it is most prevalent there and generally decreases further into the formation. When filtrate invasion occurs, it may become impossible to obtain a representative sample of formation fluids or, at a minimum, the duration of the sampling period must be increased to first remove the drilling fluid and then obtain a representative sample of formation fluids. The mudcake is made up of the solid particles that are plastered to the side of the well by the circulating drilling mud during drilling. The prevalence of the mudcake at the borehole surface creates a "skin." Thus there may be a "skin effect" because formation testers can only extend relatively short distances into the formation, thereby distorting the representative sample of formation fluids due to the filtrate. The mudcake also acts as a region of reduced permeability adjacent to the borehole. Thus, once the mudcake forms, the accuracy of reservoir pressure measurements decreases, affecting the calculations for permeability and producibility of the formation.

Another testing apparatus is the formation tester while drilling (FTWD) tool. Typical FTWD formation testing equipment is suitable for integration with a drill string during drilling operations. Various devices or systems are used for isolating a formation from the remainder of the borehole, drawing fluid from the formation, and measuring physical properties of the fluid and the formation. For example, the FTWD may use a probe similar to a WFT that extends to the formation and a small sample chamber to draw in formation fluids through the probe to test the formation pressure. To perform a test, the drill string is stopped from rotating and the test procedure, similar to a WFT described above, is performed.

Formation fluids of interest consist of liquid hydrocarbons of varying densities, typically less than that of water. On the other hand drilling fluids are usually of higher average density containing weighting material such as barite, calcium carbonate, hematite, etc. in solution or suspension. Hydrocarbon molecules consist of varying combinations of hydrogen, carbon, and oxygen atoms, resulting in fluid densities less than that of water from a few percent to several tens of percent. Borehole fluids typically are more dense than water, by factors of between one and two. Significantly higher densities than water in this range are more likely, because fluid samples are taken at target depths where the pressures are usually highest for the particular well. For the purpose of well control, the borehole fluid densities are increased to offset the effects of these downhole pressures. Usually a significant contrast between the borehole fluid density and the density of the formation fluids results.

In addition, the higher borehole fluid densities are obtained by including weighting materials mentioned above. The presence of these materials affects not only the density of the fluid but the spectral characteristics as well.

As mentioned, the representative sample of the formation fluid may be distorted by the present of filtrate and may also be distorted by the presence of borehole fluid if a proper seal is not obtained before taking the same or if the borehole fluid otherwise makes it into the sample chamber. Thus, borehole fluid is a possible "pollutant" in the early phases of the extraction, and the sample drawn from the formation should be relatively free of borehole fluid material to maintain an accurate measurement. Systems have been proposed that analyze, or identify, the sample fluid to determine the fluid identification. Such systems typically use optical sensors or sensors that measure other physical properties of the fluid. However, such systems do not necessarily provide a measure of the homogeneity of the fluid being tested.

BRIEF DESCRIPTION OF THE DRAWINGS

For a more detailed description of the embodiments, reference will now be made to the following accompanying drawings.

DETAILED DESCRIPTION OF THE EMBODIMENTS

Figure 1:
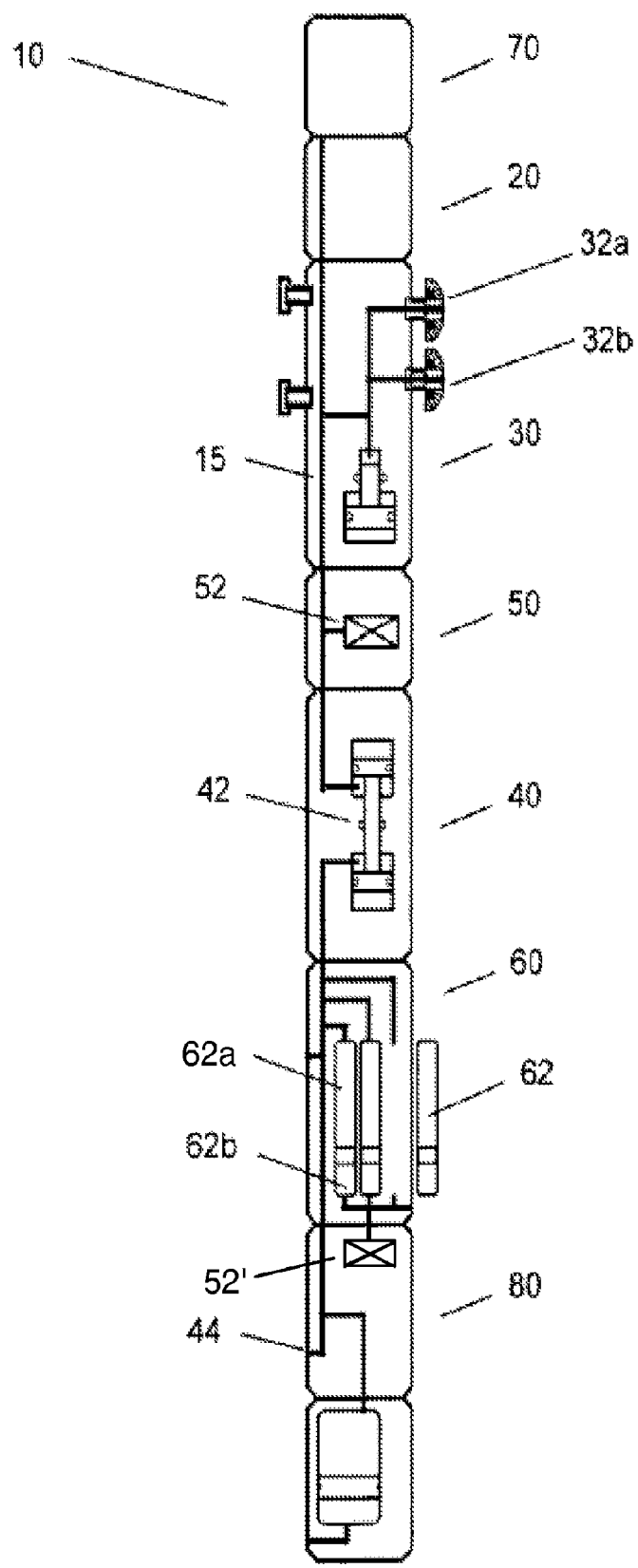
FIG. 1 is a schematic diagram of a modular downhole formation-testing tool.

In the drawings and description that follows, like parts are marked throughout the specification and drawings with the same reference numerals, respectively. The drawing figures are not necessarily to scale. Certain features of the invention may be shown exaggerated in scale or in somewhat schematic form and some details of conventional elements may not be shown in the interest of clarity and conciseness. The present invention is susceptible to embodiments of different forms. Specific embodiments are described in detail and are shown in the drawings, with the understanding that the present disclosure is to be considered an exemplification of the principles of the invention, and is not intended to limit the invention to that illustrated and described herein. It is to be fully recognized that the different teachings of the embodiments discussed below may be employed separately or in any suitable combination to produce desired results. Any use of any form of the terms "connect", "engage", "couple", "attach", or any other term describing an interaction between elements is not meant to limit the interaction to direct interaction between the elements and may also include indirect interaction between the elements described. The various characteristics mentioned above, as well as other features and characteristics described in more detail below, will be readily apparent to those skilled in the art upon reading the following detailed description of the embodiments, and by referring to the accompanying drawings.

As shown in FIG. 1, a downhole tool 10 may include a hydraulic power module 20 that converts electrical into hydraulic power; a probe module 30 to take samples of the formation fluids; a flow control module 40 regulating the flow of various fluids in and out of the tool; a fluid test module 50 for performing different tests on a fluid sample; a multi-chamber sample collection module 60 that may contain various size chambers for storage of the collected fluid samples; a telemetry module 70 that provides electrical and data communication between the modules and an uphole control unit (not shown), and possibly other sections designated in FIG. 1 collectively as 80. The arrangement of the various modules may depend on the specific application and is not considered herein.

The formation-testing tool 10 may be conveyed in the borehole by wireline, drill string, or any other suitable method. The control unit may comprise a computer and associated memory for storing programs and data. The control unit generally controls the operation of tool 10 and processes data received from it during operations. The control unit may have a variety of associated peripherals, such as a recorder for recording data, a display for displaying desired information, printers and others. The use of the control unit, display and recorder are known in the art of well logging and are, thus, not discussed further.

In a specific embodiment, telemetry module 70 may provide both electrical and data communication between the modules and the uphole control unit. In particular, telemetry module 70 provides high-speed data bus from the control unit to the modules to download sensor readings and upload control instructions initiating or ending various test cycles and adjusting different parameters, such as the rates at which various pumps are operating.

Flow control module 40 of the tool may comprise a double acting piston pump, which controls the formation fluid flow from the formation into flow line 15 via probes 32a and 32b. The pump operation is generally monitored by the uphole control unit. Fluid entering the probes 32a and 32b flows through the flow line 15 and may be discharged into the wellbore via outlet 44. A fluid control device, such as a control valve, may be connected to flow line 15 for controlling the fluid flow from the flow line 15 into the borehole. Flow line fluids can be preferably pumped either up or down with all of the flow line fluid directed into or though pump 42. Flow control module 40 may further accommodate strain-gauge pressure transducers that measure an inlet and outlet pump pressures.

The fluid testing section 50 of the tool contains a fluid testing device 52, which, analyzes the fluid flowing through flow line 15. It should be appreciated that any suitable device or devices may be utilized to analyze the fluid. For example, Halliburton Memory Recorder quartz gauge carrier can be used. In this quartz gauge the pressure resonator, temperature compensation and reference crystal are packaged as a single unit with each adjacent crystal in direct contact. The assembly is contained in an oil bath that is hydraulically coupled with the pressure being measured. The quartz gauge enables measurement of such parameters as the drawdown pressure of fluid being withdrawn and fluid temperature. Moreover, if two fluid testing devices 52 are run in tandem, the pressure difference between them can be used to determine fluid viscosity during pumping or density when flow is stopped.

Sample collection module 60 of the tool may contain various size chambers for storage of the collected fluid sample. Chamber section 60 preferably contains at least one collection chamber, preferably having a piston that divides chamber 62 into a top chamber 62a and a bottom chamber 62b. A conduit is coupled to bottom chamber 62b to provide fluid communication between bottom chamber 62b and the outside environment such as the wellbore. A fluid flow control device, such as an electrically controlled valve, can be placed in the conduit to selectively open it to allow fluid communication between the bottom chamber 62b and the wellbore. Similarly, chamber section 62 may also contain a fluid flow control device, such as an electrically operated control valve, which is selectively opened and closed to direct the formation fluid from the flow line 15 into the upper chamber 69a.

Probe module 30, and more particularly the sealing pad, comprises electrical and mechanical components that facilitate testing, sampling, and retrieval of fluids from the formation. As known in the art, the sealing pad is the part of the tool or instrument in contact with the formation or formation specimen. A probe is provided with at least one sealing pad providing sealing contact with a surface of the borehole at a desired location. Through one or more slits, fluid flow channels, or recesses in the sealing pad, fluids from the sealed-off part of the formation surface may be collected within the tester through the fluid path of the probe.

Probe module 30 generally allows retrieval and sampling of formation fluids in sections of a formation along the longitudinal axis of the borehole. The probe module 30 comprises two or more probes (illustrated as 32a and 32b), which may be located in a range of 5 cm to 100 cm apart. For example, each probe has a fluid inlet approximately 1 cm to 5 cm in diameter, for example, although other sizes may be used as well in different applications.

The fluid testing device 52 may also include as an integrated functionality or a separate unit an X-ray source and detector combination device to monitor fluid properties after entering either probe for identifying the constituents of the fluid being measured. Alternatively, the X-ray source and detector combination may be located at 52' as shown in FIG. 1 such that X-rays may be transmitted through the sample chambers 62a and 62b. Also alternatively, in the case of a radioactive isotope source, the X-ray source may be located within a sample chamber 62a or 62b with at least one detector located outside of the chamber. Also, in the case the X-ray source is electronic, the electronics that produce the electrons that impinge on the target may be located remotely within the tool 10. The availability of an X-ray source and energy sensitive detector in the downhole tool 10 enables exploitation of density differences and elemental specificity in identifying the presence of borehole fluids in downhole samples.

The use of the X-ray source and detector combination device with spectral measurements that can be made, a determination can be made of constituents (in particularly, heavy metals) in the fluid being analyzed. In addition, because it is possible to produce images using X-rays, it is possible to obtain a measure of the homogeneity of the fluid being tested.

The formation-testing tool 10 may be operated by conveying the tool 10 into the borehole to a desired location ("depth"). A hydraulic system of the tool 10 is deployed to extend rams (not shown) and probes 32a and 32b, thereby creating a hydraulic seal between the sealing pads of the probes 32a and 32b and the wellbore wall at the zone of interest. Once the sealing pad(s) and probes are set, a pretest is generally performed. The formation's permeability and isotropy can also be determined, for example, as described in U.S. Pat. No. 5,672,819, the content of which is incorporated herein by reference. Additional formation tests may also be performed that involve the collection of fluid samples through the probes 32a and 32b.

To collect the fluid samples in the condition in which such fluid is present in the formation, the area near sealing pads is flushed or pumped. The pumping rate of the double acting piston pump 42 may be regulated such that the pressure in flow line 15 near sealing pads is maintained above a particular pressure of the fluid sample. Thus, while piston pump 42 is running, the fluid-testing device 52 can measure fluid properties. The fluid-testing device 52 may provide information about the contents of the fluid and the presence of any gas bubbles in the fluid to the surface control unit 80. By monitoring the gas bubbles in the fluid, the flow in the flow line 15 can be constantly adjusted so as to maintain a single-phase fluid in the flow line 15. These fluid properties and other parameters, such as the pressure and temperature, can be used to monitor the fluid flow while the formation fluid is being pumped for sample collection.

In addition to these properties, the X-ray source and energy sensitive detector combination may be utilized to measure the physical parameters of downhole fluids. If the X-ray source is a radioactive isotope, the energy spectrum of the source may be narrow (mono-energetic). However, if the X-rays are produced using an electron beam impinging on a heavy target, e.g., tungsten, then the beam will have a distribution of energies. For this discussion, the latter type of source is used below. However, much of what is suggested here is applicable with radioactive source as well.

A first embodiment of the method of using the X-ray source fluid identifier uses the chamber containing drilling fluid from the borehole annulus or from the formation, for the purpose of obtaining measurements dependent on the density of fluid in the chamber. A collimated X-ray source is positioned such that X-rays are transmitted through the chamber, and the corresponding detector is situated on the opposite side of the chamber for detection of X-rays that are transmitted through the chamber. Alternatively, the detection site may not necessarily be of transmitted X-rays, but of scattered X-rays with the detector placed out of the direct line of the X-rays, detecting the X-rays that are scattered from the original path. In either configuration, the detected X-ray flux is a function of the density of electrons in the fluid in the chamber, and thereby also a function of the density of the fluid.

Since a goal of fluid testing is to obtain a sample of formation fluid, and to obtain a sample as uncontaminated from the drilling fluid as possible, the purity of the sample is addressed by drawing drilling fluid directly from the borehole annulus into the testing chamber. The fluid is exposed to the X-ray source for a period of time that is sufficient to obtain a statistically significant and accurate measure of the density for the material. This time will be a function of the intensity of the source and calibration characteristics of the system; however, it is straightforward for someone skilled in these measurements to determine.

As shown in FIG. 1, samples are contained in 42 and in containers 62. In addition, the apparatus can be situated outside of flow lines and used to measure density, composition and homogeneity. One possible X-ray source and detector combination device may include a chemical source of X-rays used to illuminate the fluid sample and a photodiode that is sensitive to X-rays used as the detector. However, it should be appreciated that the source could be either a chemical source of X-rays or gamma rays, or an electronic source of X-rays as, e.g., with a Crooke's tube or an X-ray tube.

This system can be used to assess qualitatively the purity of the fluid in the chamber by comparing the initial response to the borehole fluid, to the response to the fluid "produced" from the formation. As the fluid in the chamber changes from bore fluid to formation fluid, the density of fluid in the formation chamber will change. It may be that, even in the case of a perfect seal between the testing tool and the formation, a flow of uncontaminated formation fluid into the chamber may be impossible to attain. This would be due to adverse values of porosity, permeability, and insufficient mudcake on the borehole wall preventing continuous invasion of the formation. In any case the response of the X-ray system to the fluid in the chamber will be dynamic until a state of equilibrium is reached. That is, at some point one presumes that under the particular testing conditions, a maximum fraction of formation fluid will be attained in the fluid chamber. This will be indicated as the response of the X-ray system to the chamber ceases to change.

An alternative method for assessing the quality of fluid in the chamber utilizes the spectral, or energy sensitive nature of the detectors that are contemplated for use. In this embodiment, the detector will not be "in line" with the collimated X-ray source, but off to the side, at right angles, or even near 180 degree angles to the initial direction of the collimated X-rays. The utility of the method will be enhanced by the presence, particularly within the borehole fluid, of materials containing heavier, higher-Z (viz., atomic number) elements than what are the atomic constituents of hydrocarbon fluids (hydrogen, carbon, and oxygen). Examples of these elements are barium (in barite weighting material), iron (hematite), and calcium (when calcium carbonate is used).

It is noted that often the drilling fluid weighting materials are in solid, high non-soluble forms (e.g., barite) which are suspended, rather than dissolved in the drilling fluid. These materials then are largely absent in the drilling fluid contamination of the formation fluid, because they are "filtered" out during the invasion process, forming the "mud cake" on the borehole walls. The invading fluid, or "filtrate" only contains those materials which are dissolved, rather than suspended, in the drilling fluid. Consequently, high-Z materials which are present in non-soluble weighting materials are likely to be largely absent from the filtrate, reducing the effectiveness of X-ray excitation of higher-Z materials as a method for detecting the presence or absence of the filtrate. To increase this sensitivity to a "guaranteed" level, "tracer" material that is soluble in the filtrate may be added to the mud on the surface. A candidate for this material is cesium formate, which is already used in drilling muds and production fluids, but other materials are also possible.

When the detector is placed so that it will detect X-rays scattered through a higher angle, the number of X-rays detected is substantially less than when the detector is place "in line" with the incident beam. Furthermore, scattering through higher angles reduces the characteristic energy of the X-rays, as described by the Compton scattering equation. The energy and quantity of the scattered X-rays are described by the Compton and Klein-Nishina formulas respectively. The Compton shift formula is as follows:

$$\lambda' - \lambda = \frac{h}{m_e c}(1 - \cos\theta) \quad (1)$$

Where $\lambda$ is the wavelength of the photon before scattering, $\lambda'$ is the wavelength of the photon after scattering, $m_e$ is the mass of the electron, $\theta$ is the angle by which the photon's heading changes, h is Planck's constant, and c is the speed of light.

The Klein-Nishina formula is as follows:

$$\frac{d\sigma}{d\Omega} = \frac{1}{2}r_e^2(P(E_\gamma, \theta) - P(E_\gamma, \theta)^2\sin^2(\theta) + P(E_\gamma, \theta)^3) \quad (2)$$

where $\theta$ is the scattering angle; $r_e$ is the classical electron radius; $m_e$ is the mass of an electron; and $P(E_\gamma,\theta)$ is the ratio of photon energy after and before the collision:

$$P(E_\gamma, \theta) = \frac{1}{1 + \frac{E_\gamma}{m_e c^2}(1 - \cos\theta)} \quad (3)$$

In contrast the energy of the characteristic X-rays is unchanged with angle, as well as largely unaffected in intensity. This difference in the large angle scattering of X-rays will enhance the relative intensity of characteristic X-rays with respect to the Compton scattered X-rays rays. Spectral sensitivity of the detector allows discrimination of photons associated with characteristic X-ray emission from those associated with Compton scattering, and detection at appropriate angles will maximize the difference in intensity of the two types of gamma rays. Comparison of the intensities of gamma rays from these two scattering mechanisms, in conjunction with characterization of the response of the X-ray scattering from the bulk downhole fluid in the chamber, will provide a sensitive mechanism for determination of sample purity downhole.

Figure 2:
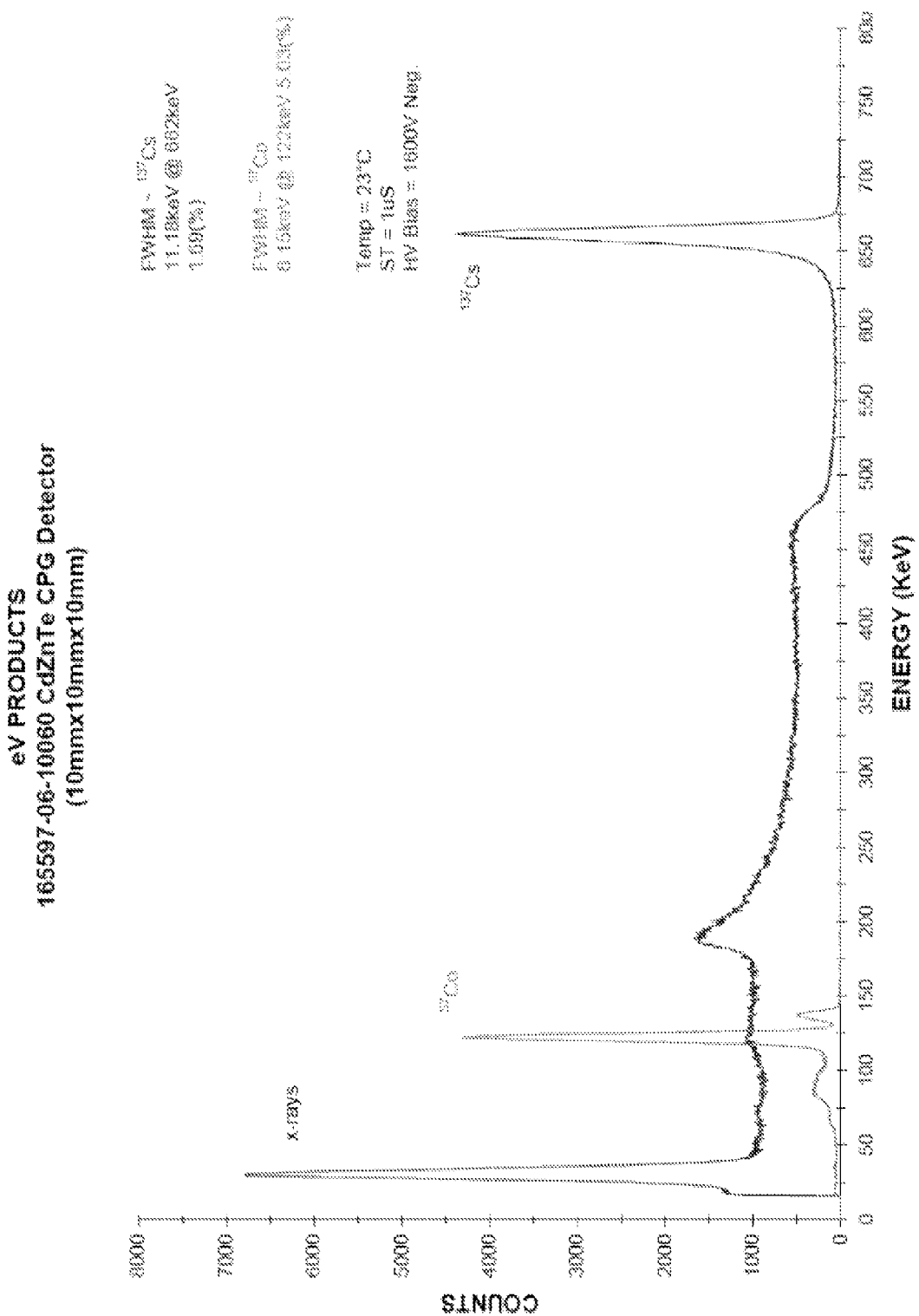
FIG. 2 is an example of a spectral response of a Cadmium Zinc Telluride (CZT) detector.

A Cadmium Zinc Telluride (CZT) detector is an example of a detector that is suitable for this application. These detectors typically have a spectral resolution of about 20 Key and are capable of operating at the elevated temperatures characteristic of wellbores. An example of a CZT detector is manufactured by eV PRODUCTS™, and a typical spectral response of a CZT detector is shown in FIG. 2.

Figure 3:
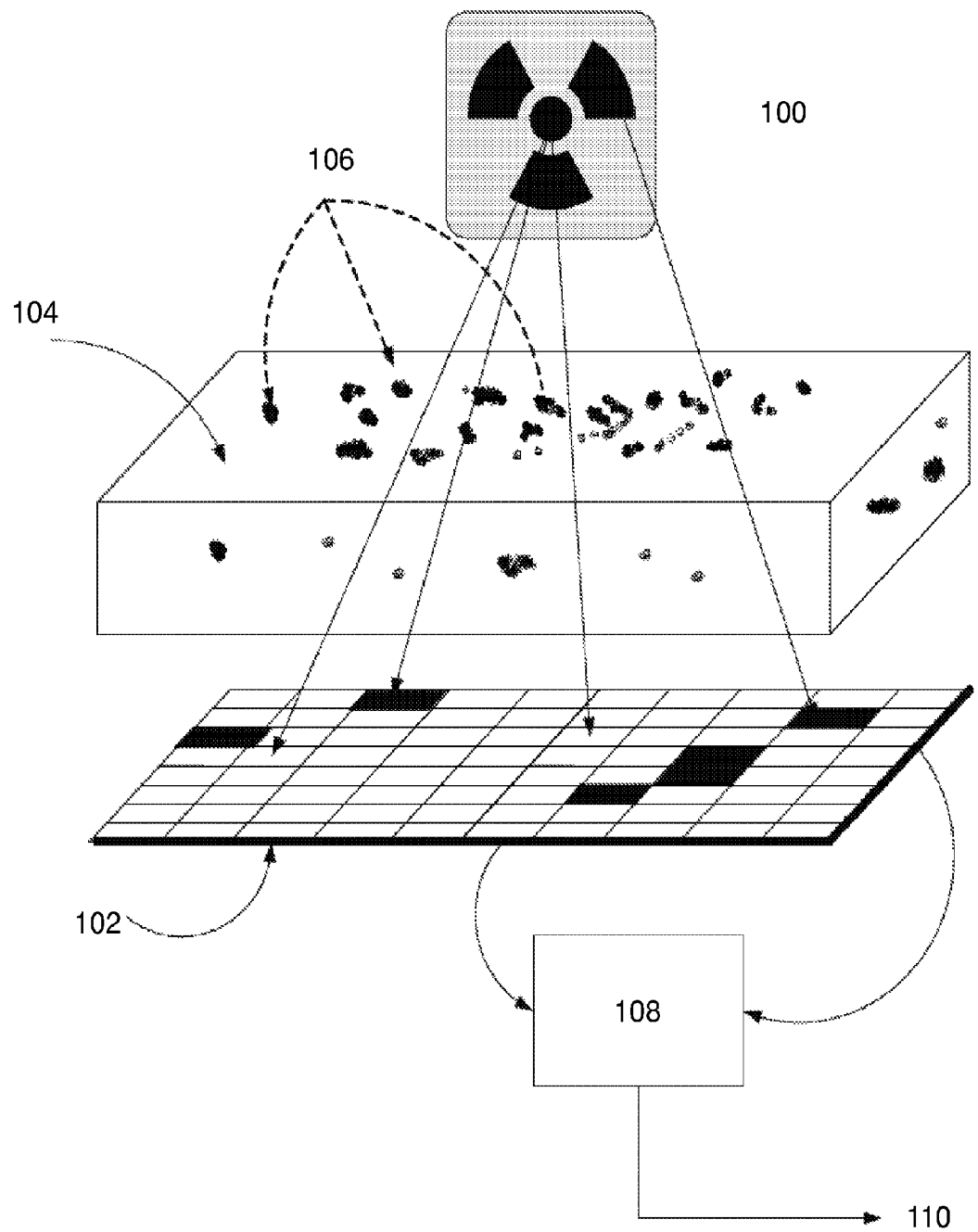
FIG. 3 is a schematic diagram of the X-RAY source and detector combination system.

Another alternative embodiment includes using the X-ray source and detection combination to detect fluid heterogeneity, where the formation fluid and/or the formation fluid is made up of two distinct materials (oil/gas/water) which are not thoroughly mixed, but form a heterogeneous composition. The differing portions of this composition might be distinguishable with X-rays using either of the methods discussed above (density or characteristic X-ray detection). In this case exposure time becomes an even more significant factor in the process if the physical distribution of the heterogeneous material is changing rapidly. This would be particularly true if the material in the flow line were being sampled. One can imagine a "plug" of material of one density passing the detector, and then a "plug" of a different material of another density passing the detector. To detect the heterogeneity, the sampling time of the detector must be on the order of or shorter than the time a particular "plug" is presented to the detector. As those skilled in the art know, the sensitivity of the detector is inversely proportional to the sampling time, and thus the sensitivity to heterogeneity will be a function of the sampling time, as well as the X-ray intensity and the density contrast or the presence or absence of excitation materials Assuming the sample in a larger test chamber is a more stable system, i.e., the differing components do not rapidly move from place to place within the chamber, another possibility is the detection of heterogeneity through the use of a two-dimensional, position sensitive detector, which in effect would function as an X-ray "camera" with an X-ray source 100 and a detector grid 102 as shown, for example, in FIG. 3. In either the density transmission or scattering case, each pixel in the "camera" functions as a measure of the intensity of X-rays traveling through a set of possible paths defined by the collimation of the X-ray source, the thickness of the test chamber, and the optical/collimation characteristics of the camera/detector. Each pixel in the camera will detect a number of photons which are an indication of the characteristic of the material in the chamber in the path of the X-rays. For example, as shown, the material may include the fluid sample 104 and impurities 106. The detector information for the sample may then be sent to a data acquisition and image processing module 108 that produces an "image" 110 of the sample for analysis. If the heterogeneity of the material in the chamber is such that its spatial variation is on the order of or larger than the dimensions of these paths, it will be possible to detect this heterogeneity through a statistical analysis of the count content of the pixels. Again the other enabling factors are the sensitivity of the method to the density differences in the different constituents of the test sample, and the sampling time used. It could be assumed that the material in the test chamber would be more stable in its location in space as a function of time than the same material in a flow line. Therefore, the sampling time for this method could be longer than for the testing in the flow line regime, with a consequent increase in sensitivity.

As an example, a typical heterogeneity measure may be performed using the following method. Let the total number of pixels in the detector array be N. Suppose further that the value that can be represented by a given pixel ranges from 0-1 (perhaps continually, but in an actual embodiment, in a finite number of increments.) The simplest measure of heterogeneity is simply the standard deviation of the values in the pixels, which is given by the following formula:

$$\overline{P} = \frac{\sum_{i=1,N} P_i}{N} \quad (4)$$

$$\sigma_P = \sqrt{\frac{\sum_{i=1,N} (P_1 - \overline{P})^2}{N-1}} \quad (5)$$

Where $P_i$ is the count in pixel I, and $\overline{P}$ is the average reading over all pixels.

More sophisticated heterogeneity measures are possible. For example, one can calculate the two-dimensional power spectral density of the image, or produce contours of the image to varying degrees of resolution, as should be familiar to one skilled in the art.

Furthermore, images can be monitored over time, so as to get a clearer picture of the dynamics of the fluid properties. In addition, because the spectral measurements can be made, a determination can be made of constituents (in particularly, heavy metals) in the fluid being analyzed.

Also, because it is possible to produce images using X-rays, it is possible to obtain a measure of the homogeneity of the fluid being tested. Making this determination in the logging while drilling environment results in significant savings, in that at least one complete bit trip and wireline logging run will be avoided.

While specific embodiments have been shown and described, modifications can be made by one skilled in the art without departing from the spirit or teaching of this invention. The embodiments as described are exemplary only and are not limiting. Many variations and modifications are possible and are within the scope of the invention. Accordingly, the scope of protection is not limited to the embodiments described, but is only limited by the claims that follow, the scope of which shall include all equivalents of the subject matter of the claims.

What is claimed is:

1. A method of determining a property of a sample of fluid, including:
    while in a borehole, collecting a sample of fluid in a downhole tool;
    while collecting the sample, emitting X-rays from an X-ray source located in the tool and transmitting the X-rays proximate to the fluid;
    collimating the X rays on a path after the X-rays are emitted from the source;
    detecting an X-ray flux from the transmitted X-rays with a detector, the flux being a function of a property of the fluid in the downhole tool; and
    while the downhole tool is in the borehole, processing the detected X-ray flux to determine the property of the fluid.

2. The method of claim 1, wherein at least a portion of the fluid sample includes formation fluid.

3. The method of claim 1, further including detecting the X-ray flux with a detector in-line with the path of the transmitted X-rays.

4. The method of claim 1, further including detecting the X-ray flux with a detector offset from the path of the transmitted X-rays, the X-ray flux including X-rays scattered from the transmitted path.

5. The method of claim 4, wherein determining the fluid property includes determining the purity of the fluid by analyzing the flux associated with characteristic X-ray emission compared to the flux associated with Compton scattering X-rays.

6. The method of claim 5, further including:
    introducing a tracer material into the borehole fluid;
    wherein collecting a sample of fluid includes collecting a sample of formation fluid; and
    determining if any of the borehole tracer material is passing into the formation by detecting any amount of the tracer material present in the sample.

7. The method of claim 1, wherein determining the fluid property includes determining the density of the fluid.

8. The method of claim 7, further including determining the density of the fluid over time and determining if the fluid density substantially equilibrates.

9. The method of claim 1 further including:
    creating the borehole through a formation using a drill bit on a drill string according to a drilling procedure;
    conveying the downhole tool into the borehole proximate the formation;
    wherein transmitting the X-rays further includes transmitting collimated X-rays proximate to the fluid on a path from the X-ray source; and
    determining whether to adjust the drilling procedure based on the determined fluid property.

10. The method of claim 9, further including detecting the X-ray flux with a detector in-line with the path of the transmitted X-rays.

11. The method of claim 9, further including detecting the X-ray flux with a detector offset from the path of the transmitted X-rays, the X-ray flux including X-rays scattered from the transmitted path.

12. The method of claim 11, wherein determining the fluid property includes determining the purity of the fluid by analyzing the flux associated with characteristic X-ray emission compared to the flux associated with Compton scattering X-rays.

13. The method of claim 12, further including:
introducing a tracer material into the borehole fluid; and
determining if any of the borehole tracer material is passing into the formation by detecting any amount of the tracer material present in the sample.

14. The method of claim 9, wherein determining the fluid property includes determining the density of the fluid.

15. The method of claim 14, further including determining the density of the fluid over time and determining if the fluid density substantially equilibrates.

16. The method of claim 9, wherein determining the fluid property includes determining the heterogeneity of the fluid.

17. The method claim 16, further including:
detecting the flux using a two-dimensional, position sensitive detector such that each position produces a count content; and
wherein determining the heterogeneity of the sample includes analyzing the count content of the positions of the detector.

18. The method of claim 16, further including determining the constituents of the fluid sample.

19. A method of determining a property of a sample of fluid, including:
while in a borehole, collecting a sample of fluid in a downhole tool;
while collecting the sample, transmitting X-rays proximate to the fluid from an X-ray source located in the tool;
detecting an X-ray flux from the transmitted X-rays with a two-dimensional, position sensitive detector such that each position produces a count content, the flux being a function of a heterogeneity of the fluid in the downhole tool; and
while the downhole tool is in the borehole, processing the detected X-ray flux to determine the heterogeneity of the fluid by analyzing the count content of the positions of the detector.

20. The method of claim 19, further including determining the constituents of the fluid sample.

21. A system used in the method of claim 1, and further including:
a formation tester conveyable downhole into the borehole, the formation tester including:
a probe engageable with a formation to form a seal and such that fluid communication between the formation and the interior of the formation tester is established;
a mechanism controlling the collection of the fluid sample through the probe and into the formation tester;
a fluid testing device including the X-ray source and the detector, the X-ray source for transmitting the X-rays and the detector for detecting the X-ray flux that is the function of the fluid property; and
a control unit including a processor for processing the detected X-ray flux to determine the fluid property.

22. The system of claim 21, wherein the X-ray source is capable of transmitting the collimated X-rays on the path.

23. The system of claim 22, further including the detector being located in-line with the X-ray transmission path.

24. The system of claim 22, further including the detector being offset from the path of the transmitted X-rays such that the detectable X-ray flux includes X-rays scattered from the transmitted path.

25. The system of claim 24, wherein the detector is capable of differentiating the flux associated with characteristic X-ray emission compared to the flux associated with Compton scattering X-rays and the determinable fluid property includes the purity of the fluid.

26. The system of claim 21, wherein the determinable fluid property includes the density of the fluid.

27. The system of claim 26, wherein the density of the fluid is capable of being determined as a function of time such that the processor is capable of determining when the fluid density substantially equilibrates.

28. The system of claim 21, wherein determinable fluid property includes the heterogeneity of the fluid.

29. The system of claim 21, wherein the determinable property includes the constituency of the fluid sample.

30. A system used in the method of claim 19, and further including:
a formation tester conveyable downhole into the borehole, the formation tester including:
a probe engageable with a formation to form a seal and such that fluid communication between the formation and the interior of the formation tester is established;
a mechanism controlling the collection of the fluid sample through the probe and into the formation tester;
a fluid testing device including the X-ray source and the two-dimensional, position sensitive detector; and
a control unit including a processor for processing the detected X-ray flux;
wherein the two-dimensional, position sensitive detector is capable of producing the count content representative of the detected flux at each position; and
wherein the processor is capable of determining the heterogeneity of the fluid by analyzing the count content of the positions of the detector.

31. A system used in the method of claim 9, and further including:
a formation tester conveyable downhole into the borehole, the formation tester including:
a probe engageable with the formation to form a seal and such that fluid communication between the formation and the interior of the formation tester is established;
a mechanism controlling the collection of the fluid sample through the probe and into the formation tester;
a fluid testing device including the X-ray source and the detector, the X-ray source for transmitting the collimated X-rays on the path and the detector for detecting the X-ray flux that is the function of the fluid property; and
a control unit including a processor for processing the detected X-ray flux to determine the fluid property.

32. The system of claim 31, further including the detector being located in-line with the X-ray transmission path.

33. The system of claim 31, further including the detector being offset from the path of the transmitted X-rays such that the detectable X-ray flux includes X-rays scattered from the transmitted path.

34. The system of claim 33, wherein the detector is capable of differentiating the flux associated with characteristic X-ray emission compared to the flux associated with Compton scattering X-rays and the determinable fluid property includes the purity of the fluid.

35. The system of claim 34, further including:
borehole fluid located in the borehole, the borehole fluid including a soluble tracer material; and
wherein the detector is capable of determining any presence of the borehole fluid tracer material in the fluid sample.

36. The system of claim 31, wherein the determinable fluid property includes the density of the fluid.

37. The system of claim 36, wherein the density of the fluid is capable of being determined as a function of time such that the processor is capable of determining when the fluid density substantially equilibrates.

38. The system of claim 31, wherein determinable fluid property includes the heterogeneity of the fluid.

39. The system claim 38, further including:
   wherein the detector includes a two-dimensional, position sensitive detector capable of producing a count content representative of the detected flux at each position; and
   wherein the processor is capable of determining the heterogeneity of the sample by analyzing the count content of the positions of the detector.

40. The system of claim 31, wherein the determinable property includes the constituency of the fluid sample.

* * * * *